United States Patent [19]

Osborne et al.

[11] Patent Number: 5,324,257
[45] Date of Patent: Jun. 28, 1994

[54] BALLOON CATHETER HAVING AN INTEGRALLY FORMED GUIDE WIRE CHANNEL

[75] Inventors: Thomas A. Osborne, Bloomington, Ind.; Arne Molgaard-Nielsen, Copenhagen,

[73] Assignee: Cook, Incorporated, Bloomington, Ind.

[21] Appl. No.: 878,036

[22] Filed: May 4, 1992

[51] Int. Cl.⁵ .................................. A61M 31/00
[52] U.S. Cl. .......................... 604/53; 604/96; 606/194
[58] Field of Search ............... 128/656–658; 604/96, 53, 280; 606/191, 192, 194

[56] References Cited

U.S. PATENT DOCUMENTS

| | | | |
|---|---|---|---|
| 4,748,982 | 6/1988 | Horzewski et al. | 128/344 |
| 4,762,129 | 8/1988 | Bonzel | 128/344 |
| 4,824,435 | 4/1989 | Giesy et al. | 604/49 |
| 4,850,358 | 7/1989 | Millar | 128/637 |
| 4,877,031 | 10/1989 | Conway et al. | 128/344 |
| 4,909,252 | 3/1990 | Goldberger | 606/194 |
| 4,928,693 | 5/1990 | Goodin et al. | 128/637 |
| 4,944,745 | 7/1990 | Sogard et al. | 606/194 |
| 4,947,864 | 8/1990 | Shockey et al. | 128/772 |
| 4,983,167 | 1/1991 | Sahota | 606/194 |
| 4,988,356 | 1/1991 | Crittenden et al. | 606/192 |
| 5,000,734 | 3/1991 | Boussignac et al. | 604/96 |
| 5,019,042 | 5/1991 | Sahota | 604/101 |
| 5,024,234 | 6/1991 | Leary et al. | 128/663.01 |
| 5,054,492 | 10/1991 | Scribner et al. | 128/662.06 |
| 5,059,177 | 10/1991 | Towne et al. | 604/96 |
| 5,078,685 | 1/1992 | Colliver | 604/96 |
| 5,084,010 | 1/1992 | Plaia et al. | 604/22 |
| 5,090,958 | 2/1992 | Sahota | 604/98 |
| 5,102,403 | 4/1992 | Alt | 604/280 |
| 5,108,366 | 4/1992 | Schatz | 604/55 |
| 5,180,367 | 1/1993 | Kontos et al. | 604/101 |

OTHER PUBLICATIONS

B. Nordenstrom, "Balloon Catheters for Percutaneous Insertion into the Vascular System," Acta Radiology, vol. 57, Nov. 1692, pp. 411–416.
B. Nordenstrom, "New Instruments for Catheterization and Angiocardiobraphy," Radiology, vol. 85 (Jul.–Dec. 1965), pp. 256–259.

Primary Examiner—C. Fred Rosenbaum
Assistant Examiner—Corrine Maglione
Attorney, Agent, or Firm—Woodard, Emhardt, Naughton, Moriarty & McNett

[57] ABSTRACT

A balloon catheter for performing angioplasty procedures includes a catheter shaft, a balloon attached to the catheter shaft near the distal end and a channel either attached to or integrally formed on the distal end of the catheter shaft distally of the balloons. The relatively short channel is threaded over a wire guide for advancing the balloon catheter into the vascular system of the patient over the wire guide. The relatively short channel allows the balloon catheter to be advanced along the wire guide with less friction interaction between the balloon catheter and wire guide than in conventional balloon catheters in which the wire guide lumen extends the full length of the catheter.

5 Claims, 5 Drawing Sheets

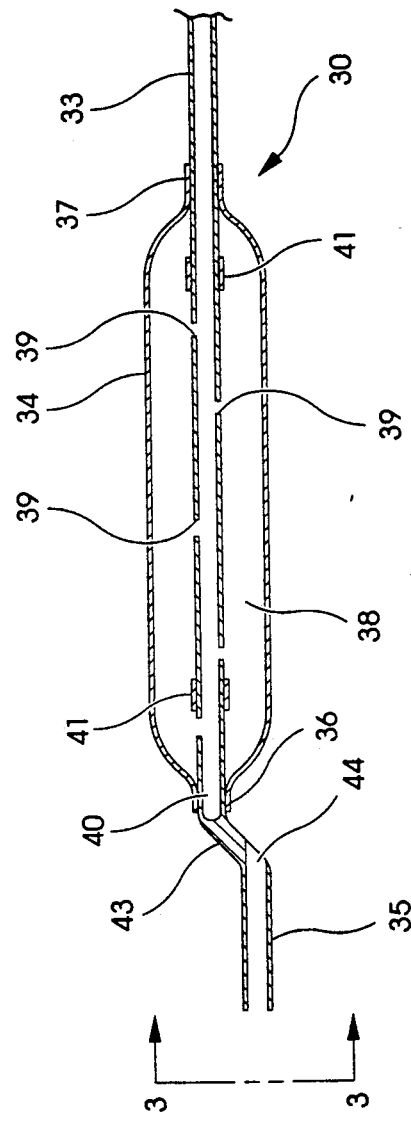
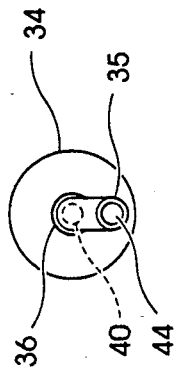
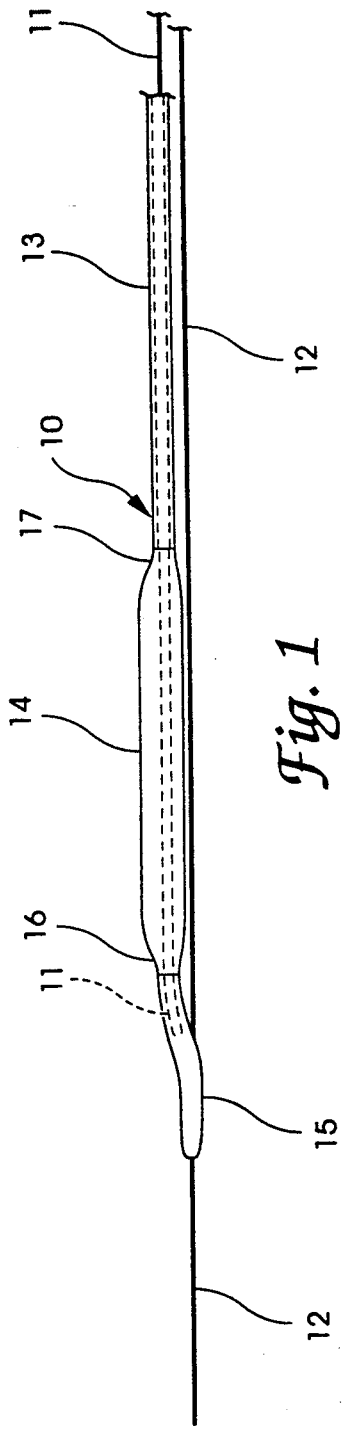

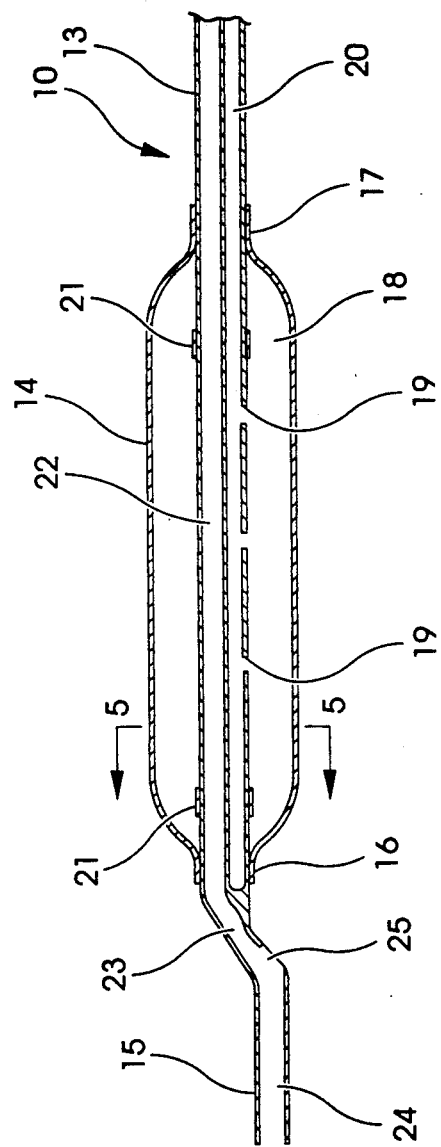
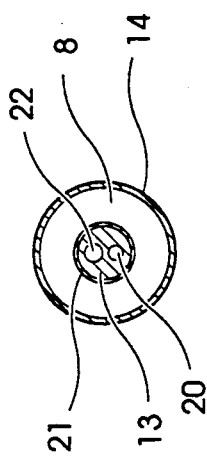

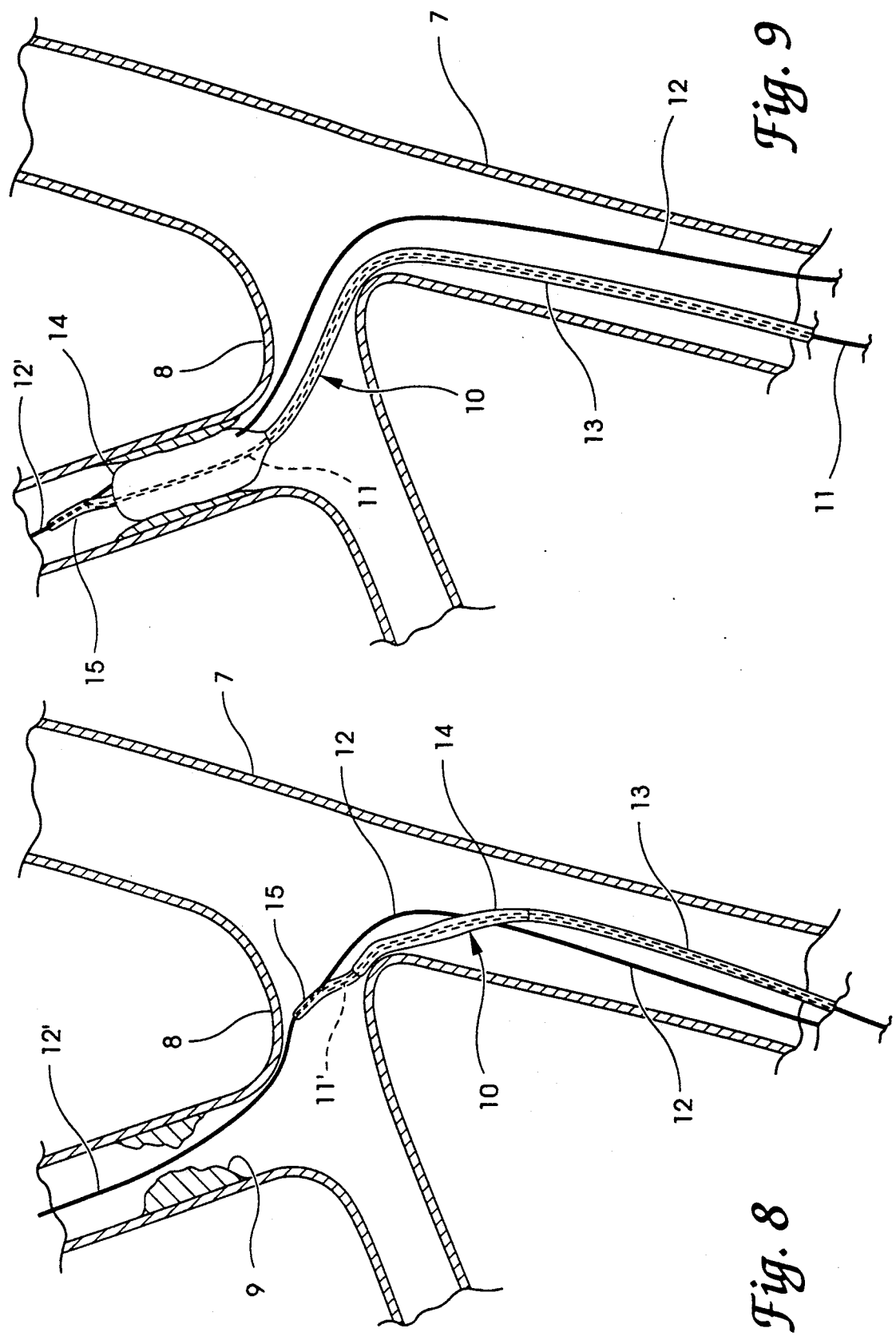

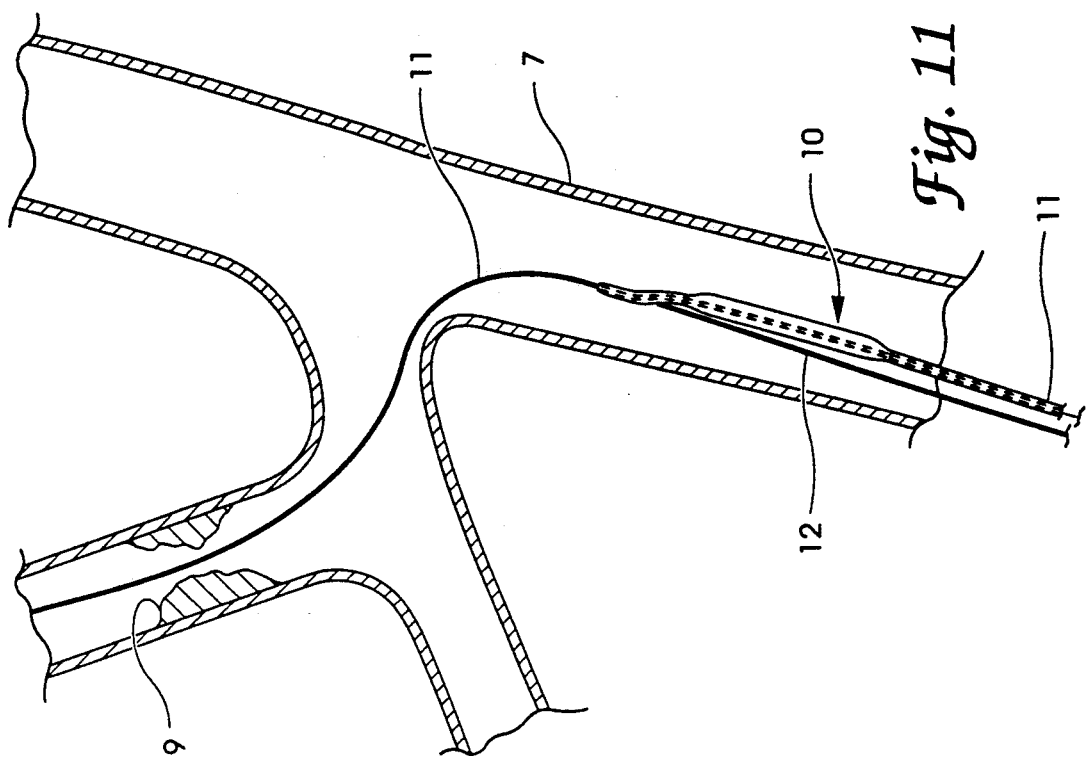
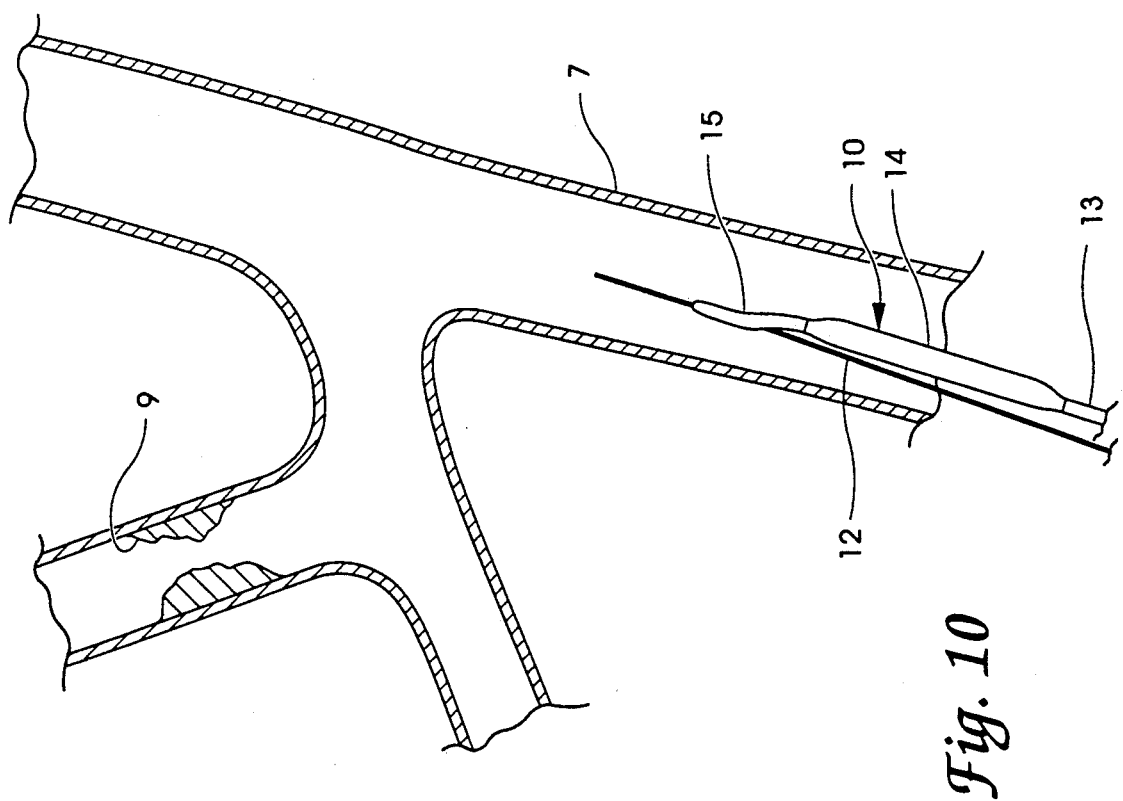

BALLOON CATHETER HAVING AN INTEGRALLY FORMED GUIDE WIRE CHANNEL

BACKGROUND OF THE INVENTION

This invention relates generally to balloon catheters and methods of using the same. In particular, this invention relates to balloon catheters for use in angioplasty procedures.

Balloon catheters generally include two lumens. One of the lumens, an inflation lumen, generally runs the length of the catheter and is in fluid communication with the balloon attached to the distal end of the catheter. This permits the balloon to readily be inflated and deflated by the application of fluid pressure at the proximal end of the catheter through the inflation lumen. A second guide wire lumen is usually provided which permits the balloon catheter to be advanced along a previously implanted wire guide to reach remote locations within the vascular system of the patient. In most balloon catheters, the guide wire lumen extends the full length of the catheter, through the interior of the balloon and out the distal end of the catheter. In order to both insert and remove the catheter while leaving the wire guide in place, is necessary that the wire guide have a length equal to at least twice that of the catheter body. Furthermore, the friction interaction of the inner surface of the catheter wire guide lumen with the wire guide tends to inhibit the performance of such catheters and often makes it more difficult for the balloon catheter to be advanced into hard-to-reach remote locations within the vascular system of the patient.

It is desirable that a balloon catheter be provided that does not require an extremely long wire guide and does not have substantial frictional interaction with the wire guide.

SUMMARY OF THE INVENTION

A balloon catheter according to one embodiment of the present invention comprises an elongate catheter shaft having a balloon secured to its distal end and an inflation lumen extending from a proximal end toward the distal end and in communication with the balloon, Also included is a relatively short wire guide channel integrally formed on the distal end of the catheter distally from where the balloon is attached to the catheter shaft, The wire guide channel is sized to slidably receive a wire guide therethrough, In use, a wire guide is advanced into the patient such that its distal end is located adjacent the area in the patient's vascular system to be dilated, The relatively short wire guide channel at the distal end of the catheter is then threaded over the proximal end of the wire guide, The balloon catheter is then simply advanced along the wire guide until the balloon is adjacent the area to be dilated, Another embodiment of a balloon catheter is also disclosed which permits the use of two wire guides to aid in the advancement of the balloon catheter to reach a desired location within a patient, This embodiment is similar to the embodiment previously described except that it also includes a wire guide lumen extending from the proximal end of the catheter shaft through the balloon and out the distal end of the catheter as in most conventional balloon catheters, However, in this embodiment, the extended wire guide lumen opens into the relatively short channel at the distal end of the catheter. This embodiment of the balloon catheter is advanced into the patient in the same way as described above except that, when the catheter reaches an area of tortuosity or has to make several direction changes that renders it difficult to advance the catheter because of its flimsiness, a second wire of any desired stiffness is passed down the extended wire guide lumen from the proximal end of the catheter to the point where the extended wire guide lumen enters the relatively short wire guide channel at the distal end of the catheter. This second wire guide gives the catheter enough stiffness or "pushability" to advance the catheter past the area of tortuosity and into very distal arteries within the patient.

Another major advantage of the arrangement for the second embodiment is that it would allow the operator to exchange one type of wire guide with another without losing the access that has already been established with the first wire guide. If the first wire guide were pulled back out of the catheter and out of the relatively short channel, the second wire can be advanced out the catheter tip in the conventional manner. The advancement of time catheter into the patient call then continue utilizing the second wire guide.

One object of the present invention is to provide an improved balloon catheter and method of using the same.

Related objects and advantages of the present invention will be apparent from the following description.

BRIEF DESCRIPTION OF THE DRAWINGS

FIG. 1 is a fragmented side elevational view of a balloon catheter according to the preferred embodiment of the present invention shown being used with two wire guides.

FIG. 2 is a fragmented sectioned side elevational view of another embodiment of the present invention.

FIG. 3 is an end view of the balloon catheter of FIG. 2 looking along arrows 3.

FIG. 4 is a fragmented sectional side elevational view of the balloon catheter shown in FIG. 1.

FIG. 5 is a cross-section through the balloon of the balloon catheter of FIG. 4 looking in the direction of arrows 5.

FIGS. 6–9 are fragmented sectioned portions of the vascular system of a patient illustrating a method of using the preferred embodiment of the present invention.

FIGS. 10 and 11 are fragmented sectioned portions of the vascular system of a patient illustrating an alternate method of using the preferred embodiment of the present invention.

DESCRIPTION OF THE PREFERRED EMBODIMENT

Figure 7:
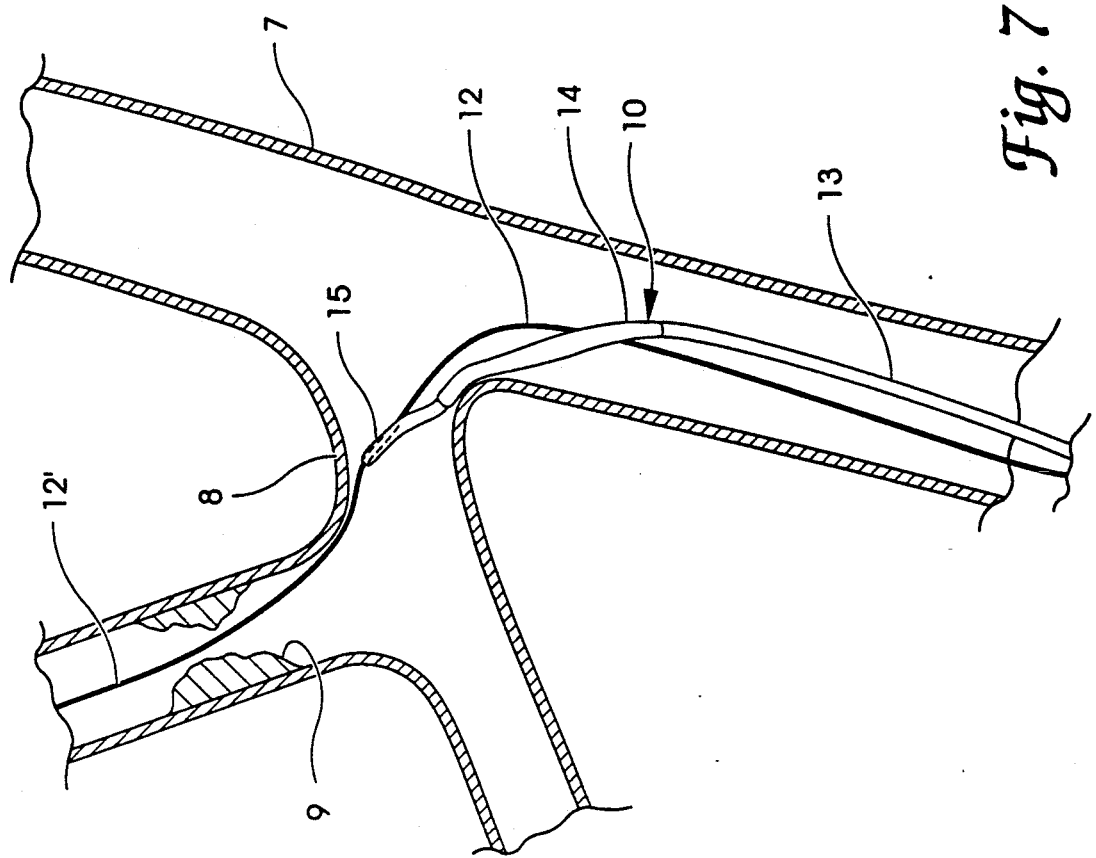

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, there is shown the distal end of a balloon catheter 10 being used in conjunction with two wire guides respectfully designated as 11 and 12. Balloon catheter 10 includes a catheter shaft 13 and a balloon 14 attached to catheter shaft 13 at its respective ends 16 and 17. Attached to, or integrally formed on, the distal end of catheter shaft 13 distally of balloon 14 is a channel 15. Wire guide 12 is slidably received into channel 15. This permits balloon catheter 10 to be either advanced or retracted on wire guide 12 simply by pushing or pulling on the proximal end (not shown) of catheter shaft 13.

FIGS. 4 and 5 are included to better illustrate the internal structure of the distal end of balloon catheter 10 shown in FIG. 1. Balloon 14 is attached at its respective ends 16 and 17 to catheter shaft 13 in a manner which is well known in the art. Two radiopaque strips 21 are attached to catheter shaft 13 within balloon 14. Strips 21 could be made from any substantially radiopaque material such as platinum or gold. Strips 21 permit the physician to determine the precise location of the balloon within the patient via X-rays. Catheter shaft 13 includes an inflation lumen 20 which extends from the proximal end (not shown) of catheter shaft 13 toward its distal end. The inflation lumen has a plugged distal end and is in fluid communication with the interior 18 of balloon 14 via a series of openings 19 within the balloon 14. Thus, balloon 14 can be inflated simply by injecting fluid along lumen 20 and through openings 19 into the interior 18 of balloon 14.

Catheter shaft 13 also includes a wire guide lumen 22 extending substantially the full length of the catheter. FIG. 1 shows a wire guide 11 extending through wire guide lumen 22 of the balloon catheter 10. Returning to FIG. 4, wire guide lumen 22 connects to lumen 24 via a connection lumen 23 at the distal end of catheter shaft 13. Lumen 24 is preferably parallel to but offset from wire guide lumen 22. Entry to lumen 24 can also be gained via side port opening 25 adjacent transition lumen 23. In this way, a wire guide can enter side pork 25, pass through lumen 24, and exit out the distal end of catheter shaft 13, as in wire guide 12 shown in FIG. 1. Alternatively, this construction allows a wire guide to be passed through wire guide lumen 22 through transition lumen 23 and on through lumen 24 out the distal end of catheter shaft 13. For instance, if wire guide 12 of FIG. 1 was retracted and disengaged from channel 15, wire guide 11 could be advanced through transition lumen 23, through lumen 24 and out the distal end of the catheter. FIG. 5 is included to illustrate the generally circular cross-sectional shape for the preferred embodiment of the present invention.

The unique structure of the balloon catheter 10 shown in FIGS. 1, 4 and 5 allows two wire guides to be utilized during the advancement procedure of the balloon catheter into the vascular system of the patient. In one method of using balloon catheter 10 shown in FIGS. 6-9 a wire guide 12 is advanced through the vascular system 7 of the patient until the distal end of wire guide 12' is within the area 9 to be dilated with the balloon 14. The channel 15 is then slidably secured over the proximal end of wire guide 12 (not shown). The balloon catheter 10 is then advanced over wire guide 12 until the catheter encounters an area of tortuosity 8 as shown in FIG. 7 that prevents the catheter 10 from being pushed any further due to its general lack of stiffness. At this point, a second wire guide 11 is advanced through wire guide lumen 22 until the distal tip of wire guide 11 has just entered into transition lumen 23 as shown in FIG. 8. Wire guide 11 provides the needed stiffness necessary to advance balloon catheter 10 past the area of tortuosity, Balloon catheter 10 and wire guide 11 are then advanced simultaneously along wire guide 12 until the catheter has successfully traversed the area of tortuosity, At this point, wire guide 11 can be withdrawn if the balloon catheter has sufficient stiffness to be advanced to the desired location. Otherwise, wire guide 11 can remain within wire guide lumen 22 for the remainder of the procedure until and after the balloon 14 arrives at the desired location 9 and is inflated as shown in FIG. 9.

In an alternative method of utilizing the balloon catheter shown in FIGS. 1, 4 and 5, a wire guide 12 is advanced into the patient only part of the way to the desired location for the dilation procedure. This method is illustrated in FIGS. 10 and 11. The channel 15 is threaded on the proximal end of wire guide 12 and then advanced into the patient until the channel 15 has been advanced beyond the distal end of wire guide and is thus "disengaged" from it. Alternatively, wire guide 12 may be withdrawn with respect to catheter 10 in order to disengage the wire guide 12 from channel 15. From this point, a second wire guide 11 is advanced through wire guide lumen 22 through transition lumen 23 and then through lumen 24 out the distal end of catheter shaft 13 until the wire guide has its distal end within the area to be dilated as shown in FIG. 11. The balloon catheter is then advanced along the second wire guide 11 until the balloon 14 is within the area to be dilated in the conventional manner. The balloon 14 is then inflated to dilate the stenotic region 9. This alternative procedure would allow the balloon to be dilated without pressing an external wire guide 12 against the artery wall. Nevertheless, it is not believed that the dilation pressures damage the wire guide 12 nor does the pressure of the balloon 14 pushing the wire 12 into the artery wall, as shown in FIG. 9, damage the artery. Thus, the second wire guide 11 can be utilized both as a stiffening member within the catheter shaft 13 (FIGS. 6-9) or as a guide wire when its distal end is advanced beyond the distal end of catheter shaft 13 (FIGS. 10 and 11).

FIGS. 2 and 3 show another embodiment of the balloon catheter 30 according to the present invention. In this case, however, balloon catheter 30 includes a catheter shaft 33 which includes only a single inflation lumen 40 therethrough. Inflation lumen 40 is similar to inflation lumen 20 discussed earlier in that it extends the full length of catheter shaft 33, but has a plugged distal end. Balloon 34 is inflated simply by injecting fluid through inflation lumen 40 through openings 39 in catheter shaft 33 and to the interior 38 of balloon 34. Balloon catheter 30 also includes radiopaque strips 41 attached to catheter shaft 33 within balloon 34. Radiopaque strips 41 are substantially identical to radiopaque strips 21 with reference to balloon catheter 10. Likewise, balloon 34 is attached to catheter shaft 33 at its respective ends 36 and 37 in a conventional manner well known in the art. Channel 35 is attached to the distal end of catheter shaft 33 by attachment portion 43. Channel 35 is preferably offset from the main inflation lumen 40 so that a wire guide extending therethrough would not interfere with the balloon 34 in order to further reduce the friction between the wire guide and the balloon catheter 30. Channel 35 can either be attached to the distal end of catheter 30, shaft 33 or be integrally formed on the distal end of catheter shaft distally beyond the balloon 34. FIG. 3 shows an end view of balloon catheter 30 shown in FIG. 2 which illustrates the preferable circular cross section of the various components.

Figure 6:
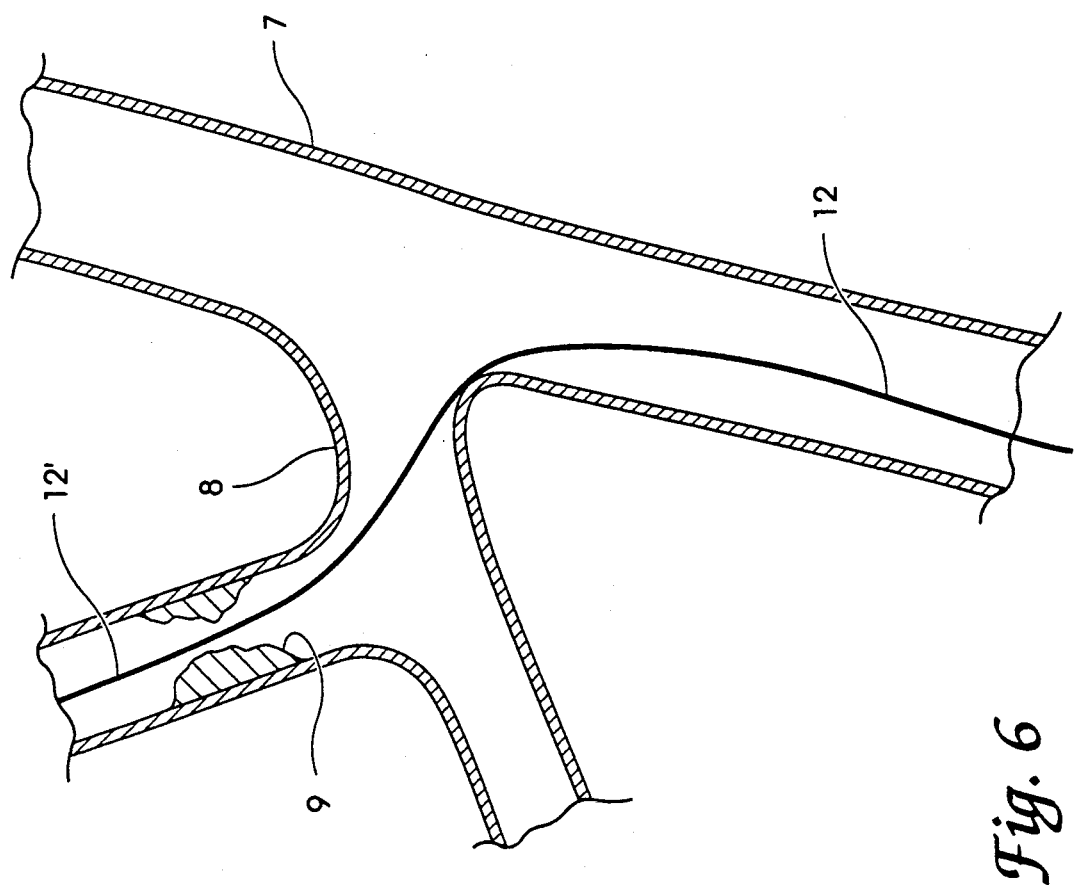

Balloon catheter 30 is used by first advancing a wire guide into the patient such that the distal end of the wire guide is near the area to be dilated as shown in FIG. 6. Next, the channel 35 is threaded over the proximal end of the wire guide and the balloon catheter 30 is simply advanced along the wire guide until tile balloon 34 is within the area to be dilated. The balloon is then inflated, and after the procedure is completed, the wire guide balloon catheter 30 are retracted from the patient. Because this embodiment of the invention includes only a single lumen, it can be made to have a significantly smaller diameter than conventional balloon catheters and therefore have the ability to be advanced through extremely narrow arteries in a patient which might otherwise be unreachable with conventional balloon catheters.

Referring back to FIG. 4, this embodiment has the further advantage that the wire guide lumen 22 can be utilized for pressure measurements or for the purpose of injecting a contrast medium. Having the channel distal to the balloon, closer to the distal end of the wire guide lumen, allows the second wire guide to advance to a position closer to the tip of the catheter where it can be used more advantageously to advance or push the catheter forward through a tight stenosis. With regard to the embodiment shown in FIG. 2, there is a possibility that a second wire guide could be used to actually push the catheter through a stenotic region by advancing a wire guide through the inflation lumen 40 until its distal end abuts the plugged distal end of the inflation lumen. In this way, the wire guide can push on the plugged distal end of the inflation lumen thus pulling the catheter along behind it as the balloon catheter 30 still remains in slidable contact with the first wire guide via the monorail channel 35.

While the invention has been illustrated and described in detail in the drawings and foregoing description, the same is to be considered as illustrative and not restrictive in character, it being understood that only the preferred embodiment has been shown and described and that all changes and raodifications that come within the spirit of the invention are desired to be protected.

What is claimed is:

1. A method of dilating a region in the vascular system of a patient comprising:
   inserting a first wire guide into the vascular system of the patient;
   providing a balloon catheter having an inflation lumen in fluid communication with a balloon secured to the catheter and a distal portion distally of the balloon that is substantially parallel to and laterally offset from the remaining portion of the catheter, and the distal portion including a first wire guide lumen therethrough, and the balloon catheter further including a second guide wire lumen extending from the proximal end and merging into the first wire guide lumen distally of the balloon;
   securing the balloon catheter to the wire guide via said first wire guide lumen;
   advancing the balloon catheter partially into the vascular system of the patient;
   stiffening the balloon catheter by advancing a second wire guide into the second wire guide lumen;
   advancing the balloon catheter until the balloon is within the area to be dilated; and
   inflating the balloon.

2. The method of claim 1 further comprising the steps of:
   withdrawing the first wire guide form the balloon catheter before the balloon has been completely advanced to the area to be dilated;
   advancing the second wire guide through the guide wire lumen and beyond the distal end of the catheter until a portion of the second wire guide is within the area to be dilated; and
   advancing the balloon catheter along the second wire guide until the balloon is within the area to be dilated.

3. A balloon catheter for use with a wire guide comprising:
   an elongate catheter shaft having a distal end portion, a proximal end and an inflation lumen extending from said proximal end toward said distal end portion;
   a balloon secured to said catheter shaft proximally of said distal end portion and in fluid communication with said inflation lumen;
   said distal end portion being laterally offset form the remaining portion of said catheter shaft and including a substantially straight first wire guide lumen extending therethrough that is substantially parallel to and laterally offset form said inflation lumen, said catheter shaft further including a second wire guide lumen extending from said proximal end to a distal end of said catheter shaft; and
   wherein said second wire guide lumen merges with said first wire guide lumen distally of said balloon.

4. A balloon catheter for use with a wire guide comprising:
   an elongate catheter shaft having a distal end, a proximal end and an inflation lumen extending from said proximal end toward said distal end;
   a balloon secured to said catheter shaft and in fluid communication with said inflation lumen;
   means, attached to said catheter shaft distally of said balloon, for slidably securing a wire guide to said catheter shaft;
   wherein said catheter shaft further includes a wire guide lumen extending form said proximal end to said distal end of said catheter shaft;
   wherein said means for slidably securing is an opening in said catheter shaft to said wire guide lumen distally of said balloon; and
   wherein said wire guide lumen includes a distal portion distal of said opening and a proximal portion, and said distal portion is offset with respect to an axis defined by said proximal portion.

5. The balloon guide of claim 4 wherein said distal portion of said wire guide lumen is substantially parallel to said axis.

* * * * *